| (12) | United States Patent<br>Watanabe et al. | (10) Patent No.: US 8,915,989 B2<br>(45) Date of Patent: Dec. 23, 2014 |
|---|---|---|

(54) POROUS COORDINATION POLYMER, PROCESS FOR PRODUCING SAME, GAS STORAGE METHOD, AND GAS SEPARATION METHOD

(75) Inventors: Daisuke Watanabe, Chiyoda-ku (JP); Shinji Oshima, Chiyoda-ku (JP); Rudy Coquet, Granieu (FR); Susumu Kitagawa, Kyoto (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 175 days.

(21) Appl. No.: 13/805,822

(22) PCT Filed: Jun. 23, 2011

(86) PCT No.: PCT/JP2011/064449
§ 371 (c)(1),
(2), (4) Date: Feb. 8, 2013

(87) PCT Pub. No.: WO2011/162351
PCT Pub. Date: Dec. 29, 2011

(65) Prior Publication Data
US 2013/0129608 A1 May 23, 2013

(30) Foreign Application Priority Data
Jun. 23, 2010 (JP) ................. 2010-142926

(51) Int. Cl.
*B01J 20/22* (2006.01)
*C07C 65/105* (2006.01)
*F17C 11/00* (2006.01)
*B01D 53/04* (2006.01)
*C07F 5/06* (2006.01)
*B01J 20/28* (2006.01)
*C07F 5/00* (2006.01)
*C07C 51/347* (2006.01)
*C07C 51/41* (2006.01)

(52) U.S. Cl.
CPC ............... *C07C 65/105* (2013.01); *F17C 11/00* (2013.01); *B01D 2253/204* (2013.01); *B01D 53/04* (2013.01); *C07F 5/069* (2013.01); *B01J 20/22* (2013.01); *B01J 20/226* (2013.01); *B01J 20/28066* (2013.01); *B01J 20/28071* (2013.01); *C07F 5/00* (2013.01); *C07F 5/06* (2013.01); *C07C 51/347* (2013.01); *Y02C 10/08* (2013.01); *C07C 51/418* (2013.01)
USPC ............................... 95/90; 502/401; 562/469

(58) Field of Classification Search
CPC .... C07C 51/418; C07C 51/347; C07C 65/05; C07C 65/105; B01J 20/22; B01J 20/226; B01J 20/28066; B01J 20/28071; C07F 5/00; C07F 5/06; C07F 5/069; Y02C 10/08; B01D 53/04; B01D 2253/202; B01D 2253/204; F17C 11/00
USPC ......... 95/90, 900; 96/108; 502/401, 402, 439; 423/648.1; 562/469
See application file for complete search history.

(56) References Cited

U.S. PATENT DOCUMENTS

| 8,500,889 B2 * | 8/2013 | Hill et al. .................. 96/153 |
| 2011/0011805 A1 * | 1/2011 | Schubert et al. .............. 210/689 |
| 2013/0139686 A1 * | 6/2013 | Wilmer et al. .................. 95/127 |
| 2014/0013943 A1 * | 1/2014 | Ryan et al. .................... 95/127 |

FOREIGN PATENT DOCUMENTS

| JP | 2003-342260 | 12/2003 |
| JP | 2005-095795 | 4/2005 |
| JP | 2006-328051 | 12/2006 |
| JP | 2006-341188 | 12/2006 |
| JP | 2007-063269 | 3/2007 |
| JP | 2007-277106 | 10/2007 |
| JP | 2008-247884 | 10/2008 |
| JP | 2009-096722 | 5/2009 |
| JP | 2009-096723 | 5/2009 |

OTHER PUBLICATIONS

International Search Reportion issued with respect to PCT/JP2011/064449, mailed Aug. 30, 2011.

English-language translation of International Preliminary Report on Patentability issued with respect to PCT/JP2011/064449, mailed Jan. 24, 2013.
Kitagawa et al., "Functional Porous Coordination Polymers", Angewandte. Chemie Intl. Ed. vol. 43, Iss. 18, pp. 2334-2375 (Apr. 26, 2004).
Japanese Office Action for JP Application No. 2010-142926, which was mailed on Jul. 29, 2014.

* cited by examiner

*Primary Examiner* — Frank Lawrence
(74) *Attorney, Agent, or Firm* — Greenblum & Bernstein, P.L.C.

(57) ABSTRACT

The porous coordination polymer of the invention contains metal complexes formed by coordination bonding between a trivalent metal ion and an aromatic tricarboxylic acid represented by formula (1). The porous coordination polymer also has a pore structure formed by integration of a plurality of the metal complexes.

[Chemical Formula 1]

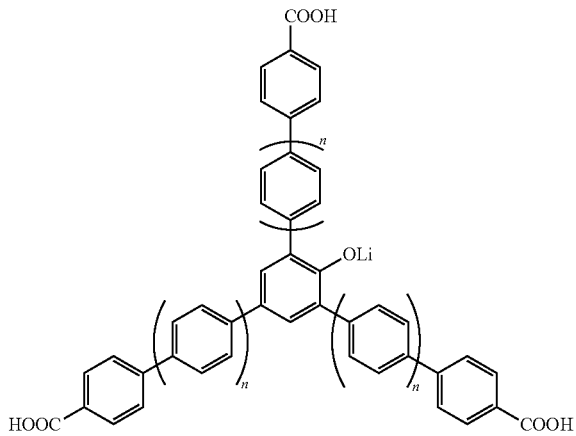

[In formula (1), n represents an integer of 0 to 4.]

7 Claims, 16 Drawing Sheets

POROUS COORDINATION POLYMER, PROCESS FOR PRODUCING SAME, GAS STORAGE METHOD, AND GAS SEPARATION METHOD

TECHNICAL FIELD

The present invention relates to a porous coordination polymer, to a process for producing it, to a gas storage method and to a gas separation method.

BACKGROUND ART

In recent years, porous coordination polymers have become a target of interest as new porous materials (see Non-patent document 1 below, for example). Porous coordination polymers are structures with pore structures formed by integration of metal complex molecules, and they are also known as integrated metal complexes (see Patent document 1, for example). Porous coordination polymers generally permit design and control of more uniform micropores than porous materials such as zeolite or active carbon.

CITATION LIST

Patent Literature

[Patent document 1] Japanese Unexamined Patent Application Publication No. 2008-247884

Non-Patent Literature

[Non-patent document 1] Angew. Chem. 2004, 43, 2334-2375.

SUMMARY OF INVENTION

Technical Problem

The present inventors first investigated porous coordination polymers employing aluminum ions, as the metal ions in porous coordination polymers. As a result, it was found that such porous coordination polymers have a high specific surface area and high pore volume. However, the porous coordination polymers still have room for improvement from the standpoint of affinity for gases (especially hydrogen gas).

It is an object of the present invention, which has been accomplished in light of these circumstances, to provide a porous coordination polymer having a high specific surface area and high pore volume, and improved affinity for gases (especially hydrogen gas), as well as a process for producing it, and a gas storage method and gas separation method using the porous coordination polymer.

Solution to Problem

According to a first aspect of the invention there is provided a porous coordination polymer. The porous coordination polymer comprises metal complexes formed by coordination bonding between a trivalent metal ion and an aromatic tricarboxylic acid represented by formula (1) below. The porous coordination polymer also has a pore structure formed by a plurality of integrated metal complexes.

[Chemical Formula 1]

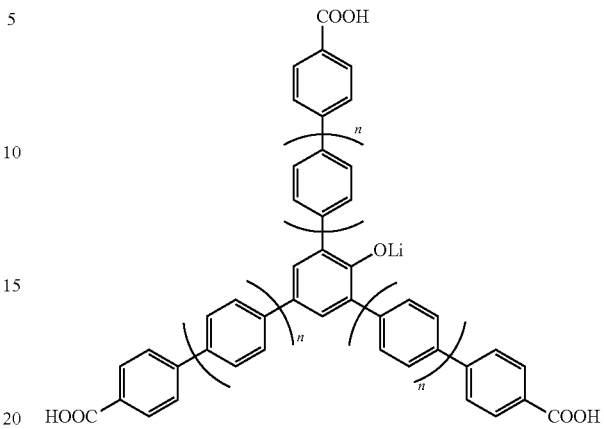

(1)

[In formula (1), n represents an integer of 0 to 4.]

According to a second aspect of the invention there is provided a process for producing a porous coordination polymer. The production process comprises a first step and a second step. In the first step, a liquid mixture is prepared comprising a trivalent metal ion, an aromatic tricarboxylic acid represented by formula (2) below, lithium hydroxide, and a co-solvent of an organic solvent and water. In the second step, the liquid mixture is heated at 100° C. or higher to obtain a porous coordination polymer comprising metal complexes formed by coordination bonding between the trivalent metal ion and the aromatic tricarboxylic acid represented by formula (1), and having a pore structure formed by integration of a plurality of the metal complexes.

[Chemical Formula 2]

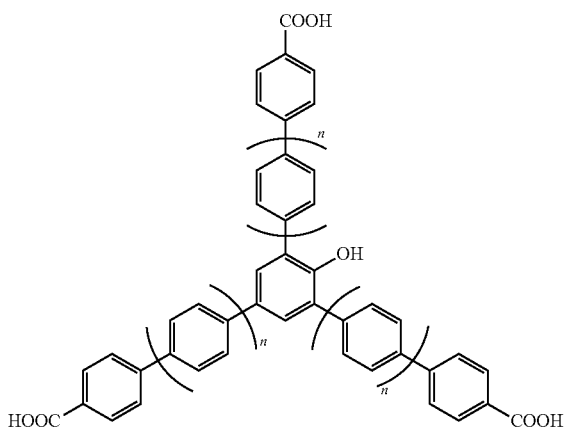

(2)

[In formula (2), n represents an integer of 0 to 4.]

According to a third aspect of the invention there is provided a process for producing a porous coordination polymer. The production process comprises a first step, a second step, a third step and a fourth step. In the first step, the aromatic tricarboxylic acid represented by formula (2) and lithium hydroxide are stirred in a co-solvent of an organic solvent and water to obtain a solution. In the second step, a trivalent metal ion solution is added dropwise to the solution obtained in the first step, to produce a precipitate. In the third step, the precipitate produced in the second step is filtered out. In the fourth step, the precipitate that has been filtered out in the third step is added to the co-solvent of an organic solvent and water and heated at 100° C. or higher to obtain a porous coordination polymer comprising metal complexes formed by coordination bonding between the trivalent metal ion and the aromatic tricarboxylic acid represented by formula (1), and having a pore structure formed by integration of a plurality of the metal complexes.

According to a fourth aspect of the invention there is provided a gas storage method. The gas storage method comprises a step of storing gas using a porous coordination polymer. The porous coordination polymer comprises metal complexes formed by coordination bonding between a trivalent metal ion and an aromatic tricarboxylic acid represented by formula (1). The porous coordination polymer also has a pore structure formed by a plurality of integrated metal complexes.

According to a fifth aspect of the invention there is provided a gas separation method. The gas separation method comprises a step of separating a gas by utilizing the difference in gas adsorption capacity of a porous coordination polymer. The porous coordination polymer comprises metal complexes formed by coordination bonding between a trivalent metal ion and an aromatic tricarboxylic acid represented by formula (1). The porous coordination polymer also has a pore structure formed by a plurality of integrated metal complexes.

Advantageous Effects of Invention

A porous coordination polymer according to the first aspect of the invention has a high specific surface area and a high pore volume, and the affinity for gases (especially hydrogen gas) is improved.

With the process for producing a porous coordination polymer according to the second aspect and third aspect of the invention, it is possible to more easily obtain a porous coordination polymer having a high specific surface area and a high pore volume, and improved affinity for gases (especially hydrogen gas). The production process is also preferred for increasing the amount of Li introduced.

With the gas storage method according to the fourth aspect of the invention, it is possible to store more gas (especially hydrogen gas) in a given volume.

With the gas separation method according to the fifth aspect of the invention, it is possible to store relatively more of a desired gas at a prescribed temperature. That is, the gas separation method is suitable for selectively separating a desired gas from a mixed gas that contains the desired gas.

DESCRIPTION OF EMBODIMENTS

Figure 1:
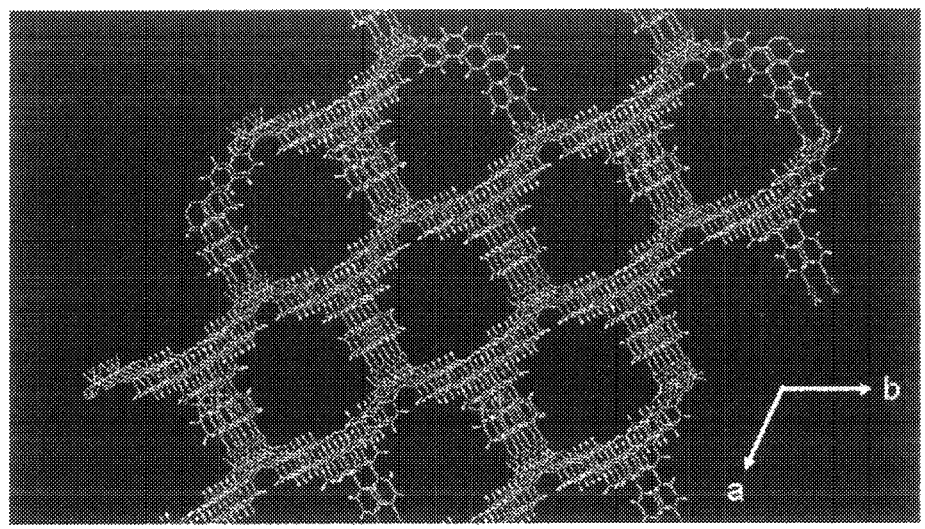
FIG. 1 is a diagram showing the crystal structure of [Al($C_{27}H_{14}O_7Li$)] based on MSINDO calculation.

Preferred embodiments of the invention will now be explained.

The porous coordination polymer according to this embodiment comprises metal complexes formed by coordination bonding between a trivalent metal ion and an aromatic tricarboxylic acid represented by formula (1) above. Examples of trivalent metal ions include aluminum(III) ion, iron(III) ion, chromium(III) ion, scandium(III) ion, gallium (III) ion, yttrium(III) ion, indium(III) ion, lanthanum(III) ion, cerium(III) ion, praseodymium(III) ion, neodymium(III) ion, promethium(III) ion, samarium(III) ion, europium(III) ion, gadolinium(III), terbium(III) ion, dysprosium(III) ion, holmium(III) ion, erbium(III) ion, thulium(III) ion, ytterbium (M) ion and lutetium(III) ion. Aluminum ion is preferred from the viewpoint of increasing hydrogen storage capacity, while terbium ion or iron(III) ion is preferred from the viewpoint of facilitating production. The aromatic tricarboxylic acid represented by formula (1) has lithium (Li) introduced therein.

The porous coordination polymer of this embodiment may include the aromatic tricarboxylic acid represented by formula (1) as a ligand in at least a portion thereof. The aromatic tricarboxylic acid represented by formula (1) and another ligand such as an aromatic tricarboxylic acid represented by formula (2) above, may both be present in the porous coordination polymer of this embodiment. When an aromatic tricarboxylic acid represented by formula (1) and the aforementioned other ligand are both present, the proportion of the aromatic tricarboxylic acid represented by formula (1) may be appropriately adjusted according to the type of gas, so that the storage volume of gas per unit volume is further increased.

The porous coordination polymer of this embodiment has a pore structure. The method of controlling the pore size or pore volume of the pore structure, for easy control, may be a method of varying the n number of the aromatic tricarboxylic acid represented by formula (1), and the pore size or pore volume increases as the n number increases. Here, n is preferably at least 2 and no greater than 4 from the viewpoint of increasing the gas storage capacity for gases such as nitrogen ($N_2$), oxygen ($O_2$), argon (Ar), carbon dioxide ($CO_2$), nitrogen monoxide (NO), carbon monoxide (CO) or methane ($CH_4$), and forming a suitable pore structure. From the viewpoint of increasing the hydrogen gas storage capacity, n is preferably no greater than 2. Particularly from the viewpoint of both reducing synthesis cost and facilitating production, it is preferably no greater than 1.

The pores are formed by integration of a plurality of metal complexes formed by coordination bonding between a trivalent metal ion and an aromatic tricarboxylic acid represented by formula (1). The shapes of the pores are hexagonal, as viewed in the direction of gas approach.

In the porous coordination polymer of this embodiment, the pore structures are formed by integration of a plurality of metal complexes formed by coordination bonding between the trivalent metal ion and an aromatic tricarboxylic acid represented by formula (1). Also, the porous coordination polymer of this embodiment may include the aromatic tricarboxylic acid represented by formula (1) as a ligand. Thus, a porous coordination polymer according to this embodiment has a high specific surface area and a high pore volume, and the affinity for gases (especially hydrogen gas) is improved. A porous coordination polymer according to this embodiment therefore has high storage capacity for gases (especially hydrogen gas).

In a porous coordination polymer according to this embodiment, the pore volume is preferably at least 0.1 $cm^3$ per gram of the porous coordination polymer. With such a structure, it is possible to ensure a hydrogen storage capacity of 0.1 wt % or greater in a prescribed atmosphere (for example, temperature: 303K, hydrogen pressure: 10 MPa).

A porous coordination polymer according to this embodiment may further comprise metal complexes formed by coordination bonding between a trivalent metal ion and an aromatic tricarboxylic acid represented by formula (2) above. With such a structure, it is possible to increase the adsorption capacity for gases with intramolecular polarization, such as $CH_4$ and $CO_2$, compared to a metal complex formed using an aromatic tricarboxylic acid without a hydroxyl group as the ligand.

A porous coordination polymer according to this embodiment can be produced by the first and second production processes described below. However, the process for producing the porous coordination polymer of this embodiment is not limited to the following. The first and second production processes will now each be explained.

(First Production Process)

The first production process comprises a step A and a step B.

In step A, a liquid mixture is prepared comprising a trivalent metal ion, an aromatic tricarboxylic acid represented by formula (2), lithium hydroxide, and a co-solvent consisting of an organic solvent and water.

For preparation of the liquid mixture in step A, the trivalent metal ion is supplied as a metal salt containing the trivalent metal ion at a prescribed concentration (for example, between 10 mmol/L and 100 mmol/L). Various compounds may be employed as the metal salt, but nitric acid salts are preferred from the viewpoint of solubility in organic solvents. The amount of trivalent metal ion supplied may be appropriately set depending on the type of liquid mixture. The amount of trivalent metal ion supplied is preferably in the range of 0.75 to 4 equivalents, and more preferably in the range of 1 to 2 equivalents, with respect to the aromatic tricarboxylic acid represented by formula (2). The trivalent metal ion used may be any of those mentioned above.

For preparation of the liquid mixture in step A, the aromatic tricarboxylic acid represented by formula (2) is supplied in the form of a solution or solid (for example, a powder) of prescribed purity (for example, 90 mass % or greater). The concentration of the aromatic tricarboxylic acid represented by formula (2) in the liquid mixture in step A may be appropriately set depending on the type of liquid mixture, and it is preferably between 10 mmol/L and 100 mmol/L. An example for synthesis of an aromatic tricarboxylic acid represented by formula (2) where n is zero will now be described.

First, a mixture is obtained by combining 2,4,6-tribromophenol, 4-(methoxycarbonyl)-phenylboronic acid, sodium carbonate, palladium dichlorobistriphenylphosphine, water and N,N-dimethylformamide under a nitrogen gas atmosphere. The mixture is stirred at between 50° C. and 100° C. for at least 5 hours and no longer than 15 hours. After stirring, water is added to the mixture and concentrated hydrochloric acid is added to render the solution acidic and produce crystallization. The obtained crystals are filtered out, rinsed with methanol and purified by column chromatography. The obtained purified product is recrystallized from methanol to obtain 2,4,6-tris(4-methoxycarbonyl)phenol. Next, the 2,4,6-tris(4-methoxycarbonyl)phenol is mixed with potassium hydroxide, water and methanol and the mixture is refluxed for between 5 and 15 hours. Upon completion of the reaction, concentrated hydrochloric acid is added to the reaction mixture to render it acidic, and the deposited white precipitate is filtered out, rinsed with water and methanol and dried. This yields an aromatic tricarboxylic acid represented by formula (2), where n is 0.

For preparation of the liquid mixture in step A, the lithium hydroxide is supplied as a solution or a solid (powder) of a prescribed purity (for example, 90 mass % or greater). The amount of lithium hydroxide supplied may be appropriately set depending on the desired liquid mixture, but it is preferably at least 1 equivalent, and more preferably in the range of 2 to 6 equivalents, with respect to the aromatic tricarboxylic acid represented by formula (2).

The organic solvent used to prepare the liquid mixture in step A may be N,N-dimethylformamide, N,N-diethylformamide, dimethyl sulfoxide, cyclohexanol or the like. When aluminum ion is used as the trivalent metal ion it is preferred to use N,N-dimethylformamide or N,N-diethylformamide, and when terbium ion is used as the trivalent metal ion it is preferred to use cyclohexanol.

In step B, the liquid mixture is heated at 100° C. or higher to obtain a porous coordination polymer comprising metal complexes formed by coordination bonding between the trivalent metal ion and the aromatic tricarboxylic acid represented by formula (1), and having a pore structure formed by integration of a plurality of the metal complexes.

The temperature of the liquid mixture in step B is set to 100° C. or higher (more preferably 120° C. or higher), from the viewpoint of satisfactorily generating the desired porous coordination polymer. The temperature of the liquid mixture in step B is also preferably set to be no higher than 150° C. from the viewpoint of limiting decomposition of organic solvents such as N,N-dimethylformamide and N,N-diethylformamide.

Heating of the liquid mixture in step B may be carried out in an air atmosphere. The heating of the liquid mixture is preferably carried out in a sealed reactor such as an autoclave, from the viewpoint of yield.

The porous coordination polymer of this embodiment, which is produced in the liquid mixture obtained from step B, may be obtained by filtering from the liquid mixture and rinsing with an organic solvent such as N,N-dimethylformamide or N,N-diethylformamide.

With the first production process according to this embodiment, it is possible to more easily obtain a porous coordination polymer having a high specific surface area and a high pore volume, and improved affinity for gases (especially hydrogen gas). This production process is also preferred from the viewpoint of increasing affinity for especially hydrogen gas, and satisfactorily increasing the amount of Li introduced.

(Second Production Process)

The second production process comprises a step C, a step D, a step E and a step F.

In step C, the aromatic tricarboxylic acid represented by formula (2) and lithium hydroxide are stirred in a co-solvent of an organic solvent and water to obtain a solution.

For preparation of the solution in step C, the aromatic tricarboxylic acid represented by formula (2) is supplied in the form of a solution or solid (for example, a powder) of prescribed purity (for example, 90 mass % or greater). The concentration of the aromatic tricarboxylic acid represented by formula (2) in the liquid mixture in step C may be appropriately set, and it is preferably between 10 mmol/L and 100 mmol/L.

For preparation of the solution in step C, the lithium hydroxide is supplied as a solution or a solid (for example, powder) of a prescribed purity (for example, 90 mass % or greater). The amount of lithium hydroxide supplied may be appropriately set depending on the type of liquid mixture. The amount of lithium hydroxide supplied is preferably an addition at 1 or more equivalents, and more preferably an addition in the range of 2 to 6 equivalents, with respect to the aromatic tricarboxylic acid represented by formula (2).

The organic solvent used to prepare the solution in step C may be ethanol, methanol, tetrahydrofuran, N,N-dimethylformamide, cyclohexanol or the like. From the viewpoint of solubility, N,N-dimethylformamide is especially preferred.

In step D, a trivalent metal ion solution is added dropwise to the solution obtained in step C, to produce a precipitate.

The trivalent metal ion to be added dropwise in step D is supplied as a solution of a metal salt containing the trivalent metal ion at a prescribed concentration (for example, between 10 mmol/L and 100 mmol/L). Various compounds may be employed as the metal salt, but nitric acid salts are preferred from the viewpoint of solubility in organic solvents. The amount of trivalent metal ion supplied may be appropriately set depending on the desired liquid mixture, but it is preferably an addition at between 0.75 and 4 equivalents and more preferably an addition at between 1 and 2 equivalents, with respect to the aromatic tricarboxylic acid represented by formula (2). The trivalent metal ion used may be any of those mentioned above.

In step E, the precipitate produced in step D is filtered out.

In step F, the precipitate that has been filtered out in step E is added to the co-solvent of an organic solvent and water and heated at 100° C. or higher to obtain a porous coordination polymer comprising metal complexes formed by coordination bonding between the trivalent metal ion and the aromatic tricarboxylic acid represented by formula (1), and having a pore structure formed by integration of a plurality of the metal complexes.

The organic solvent in step F may be the same organic solvent used in step C.

The temperature of the co-solvent in step F is set to 60° C. or higher (more preferably 120° C. or higher), from the viewpoint of satisfactorily generating the desired porous coordination polymer. The temperature of the co-solvent in step F is preferably set to be no higher than 150° C., from the viewpoint of limiting decomposition of the organic solvent.

Heating of the co-solvent in step F may be carried out in an air atmosphere. The heating of the co-solvent is preferably carried out in a sealed reactor such as an autoclave, from the viewpoint of yield.

The porous coordination polymer of this embodiment, which is produced in the co-solvent obtained from step F, may be obtained by filtering from the co-solvent and rinsing with an organic solvent such as N,N-dimethylformamide or N,N-diethylformamide.

With the first production process according to this embodiment, it is possible to more easily obtain a porous coordination polymer having a high specific surface area and a high pore volume, and improved affinity for gases (especially hydrogen gas). This production process is also preferred from the viewpoint of increasing the amount of Li introduced so as to increase affinity for especially hydrogen gas.

A gas storage method according to this embodiment will now be explained.

The aforementioned gas storage method employs a porous coordination polymer according to the embodiment described above. For example, when the gas that is to be stored is $N_2$, $O_2$, Ar, $CO_2$, NO, CO, $CH_4$ or the like, the porous coordination polymer is preferably one in which n in the aromatic tricarboxylic acid represented by formula (1) is between 2 and 4. When the purpose is storage of hydrogen gas, the porous coordination polymer used is preferably one in which n in the aromatic tricarboxylic acid represented by formula (1) is no greater than 2.

In the gas storage method described above, a porous coordination polymer produced by any of the production processes described above, for example, may be used directly. However, it is preferably subjected to pretreatment to more satisfactorily remove solvent molecules present in the pore structure. Such pretreatment may be drying in a temperature range in which the porous coordination polymer does not undergo any substantial decomposition, and rinsing with supercritical $CO_2$. Rinsing with supercritical $CO_2$ is preferred from the viewpoint of increasing the removal effect for the solvent molecules. The temperature range for drying may be between 25° C. and 250° C., for example. This temperature range is most preferably between 100° C. and 180° C. from the viewpoint of increasing the removal effect for the solvent molecules and limiting decomposition of the complex structure.

With the gas storage method of this embodiment, it is possible to store more gas (especially hydrogen gas) in a given volume, and to further increase the storage effect by the aforementioned pretreatment.

A gas separation method according to this embodiment will now be explained.

The gas separation method comprises a step of separating a gas by utilizing the difference in gas adsorption capacity by a porous coordination polymer. The porous coordination polymer used is a porous coordination polymer according to the embodiment described above. The difference in gas adsorption capacity is the difference between the gas adsorption capacity of a gas that is to be adsorbed and the gas adsorption capacity for a gas that is not to be adsorbed. In order to increase the purity of gas separation in the gas separation method, the gas adsorption capacity for the gas that is not to be adsorbed is preferably set to essentially 0 (zero), and more preferably it is set so that the aforementioned difference in gas adsorption capacity is large. For example, when hydrogen gas is to be selectively adsorbed from a mixed gas comprising hydrogen gas, a porous coordination polymer according to the embodiment described above may be one wherein n is no greater than 2.

With the gas separation method of this embodiment, it is possible to store relatively more of a desired gas at a given temperature. That is, the gas separation method is suitable for selectively separating a desired gas from a mixed gas that contains the desired gas. By this gas separation method, therefore, it is possible to accomplish separation of a mixed gas into separate gases utilizing the difference in adsorption capacity due to differences in the structure of a porous coordination polymer.

The embodiment described above is only a preferred embodiment of the invention, and the invention is in no way limited thereto.

EXAMPLES

The present invention will now be explained in greater detail based on examples and comparative examples, with the understanding that these examples are in no way limitative on the invention.

Example 1

Porous Coordination Polymer Comprising Aluminum Ion and Aromatic Tricarboxylic Acid Represented by Formula (3)

[Chemical Formula 3]

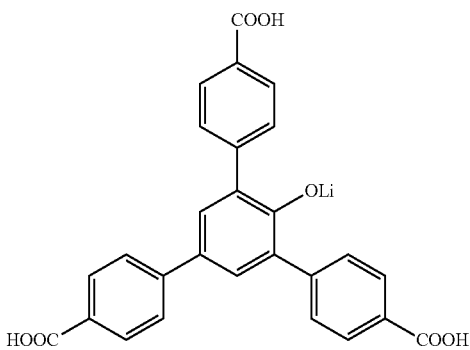

(3)

(Synthesis of Aromatic Tricarboxylic Acid Represented by Formula (4))

A compound represented by formula (4) was synthesized by the following steps 1-1 and 1-2.

[Chemical Formula 4]

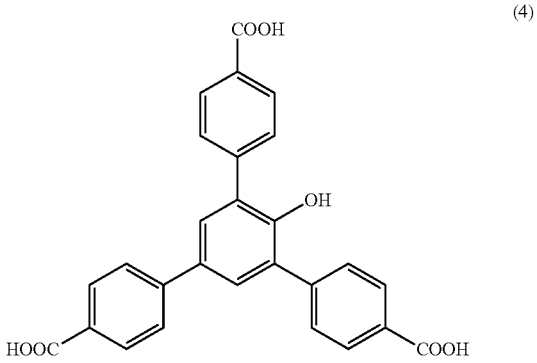

(4)

Step 1-1: Synthesis of 2,4,6-tris-(4-methoxycarboxyphenyl)phenol

After placing N,N-dimethylformamide by Godo Co., Ltd. (1000 mL) and water (670 mL) in a reactor, the mixture was bubbled with argon gas for 30 minutes to remove the dissolved oxygen. To the mixed solvent of N,N-dimethylformamide and water in the reactor there were added 2,4,6-tribromophenol by Tokyo Kasei Kogyo Co., Ltd. (167.00 g), 4-(methoxycarbonyl)-phenylboronic acid by Sigma-Aldrich Corp. (299.82 g), sodium carbonate by Nacalai Tesque, Inc. (256.84 g) and palladium dichlorobistriphenylphosphine by N.E. Chemcat Corp., under an argon atmosphere, and the components were heated and stirred at 60° C. to obtain a reaction mixture. By monitoring the reaction by TLC (thin-layer chromatography) after 12 hours, disappearance of the starting material was confirmed.

After allowing the reaction mixture to cool to room temperature, purified water (7 L) was added to the reaction mixture, and then concentrated hydrochloric acid was added to adjust the pH of the reaction mixture to 2 (Univ). The precipitated crystals were filtered out and dispersed and rinsed with methanol (1.5 L) for 30 minutes. The crystals were then filtered out and dried to obtain 319.74 g of a crude product. This was purified with a silica gel column (φ: 110 mm, weight: 2200 g, developing solvent: chloroform) to obtain a concentrated residue. After adding methanol to the obtained concentrated residue, it was filtered and dried to obtain 187.42 g of a white solid (2,4,6-tris-(4-methoxycarboxyphenyl)phenol) as the target compound. (Yield: 74.8 wt %)

The $^1$H-NMR results for the obtained 2,4,6-tris-(4-methoxycarboxyphenyl)phenol were as follows.

$^1$H-NMR (300 MHz, CDCl$_3$): δ=8.17 (d, J=8.2 Hz, 4H, Ar), 8.09 (d, J=8.2 Hz, 2H, Ar), 7.69 (d, J=8.2 Hz, 4H, Ar), 7.68 (d, J=8.2 Hz, 2H, Ar), 7.59 (s, 2H, Ar), 5.50 (s, 1H$_2$OH), 3.95 (s, 6H, COOCH$_3$), 3.93 (s, 3H, COOCH$_3$)

Step 1-2: Synthesis of 2,4,6-tris-(4-carboxyphenyl)phenol

In a reactor there were placed 2,4,6-tris(4-methoxycarbonyl)phenol (187.00 g), potassium hydroxide by Kanto Kagaku Co., Ltd. (76.08 g) and purified water (1870 mL), and the mixture was stirred for 2 hours while heating to reflux to obtain a reaction mixture. The reaction mixture was then subjected to TLC to monitor the reaction. It was thus confirmed that the 2,4,6-tris(4-methoxycarbonyl)phenol starting material had disappeared. After allowing the reaction mixture to cool to room temperature, the insoluble portion was filtered out. Concentrated hydrochloric acid was added dropwise to the obtained mother liquor while cooling on ice, to adjust the pH to 2 (Univ). The precipitated crystals were centrifuged (rotational speed: 3100 rpm, time: 5 minutes, temperature: 4° C.) and the mother liquor was removed. Next, the obtained wet crystals were rinsed 5 times with purified water and dried with forced air at 60° C. for 18 hours. The obtained crystals were pulverized with a mortar to obtain powder crystals. The powder crystals were dispersed and rinsed with isopropyl ether and dried, to obtain 151.83 g of a faint brown powder (2,4,6-tris-(4-carboxyphenyl)phenol) as the target compound. (Yield: 88.8 wt %)

The $^1$H-NMR, $^{13}$C-NMR and MS results for the obtained 2,4,6-tris-(4-carboxyphenyl)phenol were as follows.

$^1$H-NMR (300 MHz, DMSO-$d_6$): δ=12.93 (bs, 2H, COOH), 8.95 (bs, 1H, COOH), 8.02 (d, J=8.2 Hz, 4H, Ar), 7.98 (d, J=8.4 Hz, 2H, Ar), 7.88 (d, J=8.4 Hz, 2H, Ar), 7.77 (d, J=8.2 Hz, 4H, Ar), 7.65 (s, 2H, Ar)

$^{13}$C-NMR (300 MHz, DMSO-$d_6$): δ=167.26 (COOH), 167.19 (COOH), 151.15 (Ar), 143.69 (Ar), 142.81 (Ar), 131.60 (Ar), 130.83 (Ar), 129.90 (Ar), 129.72 (Ar), 129.43 (Ar), 129.26 (Ar), 129.09 (Ar), 128.91 (Ar), 126.74 (Ar)

MS: m/z=454.18 (M)

(Synthesis of Porous Coordination Polymer)

Aluminum nitrate nonahydrate by Kishida Chemical Co., Ltd. (1.72 g, 4.6 mmol) and 2,4,6-tris-(4-carboxyphenyl)phenol (1.04 g, 2.3 mmol) were each placed in a screw tube. A mixed solvent comprising N,N-dimethylformamide by Kanto Kagaku Co., Ltd. (1 mL) and purified water (1.25 mL) was added to each screw tube. The screw tubes were dipped in an ultrasonic cleaner for several minutes to form a homogeneous solution.

The two solutions were then combined and placed in a TEFLON® crucible by San-Ai Science Co., Ltd. Lithium hydroxide by Wako Pure Chemical Industries, Ltd. (221 mg, 9.2 mmol) was added to the crucible. The crucible was mounted in an autoclave by San-Ai Science Co., Ltd. and subjected to hydrothermal synthesis at 120° C. for 10 hours, and then allowed to stand overnight. On the following day it was filtered, and the obtained solid was rinsed with a mixed solvent comprising N,N-dimethylformamide and purified water in equal weights. This was followed by 30 minutes of vacuum drying to obtain a white product. (Yield: 2.21 g)

(Structure of Porous Coordination Polymer)

Using the Cif file for [Tb($C_{27}H_{15}O_6$)], reported in J. Am. Chem. Soc. 2005, 127, 12788-12789, MSINDO calculation was performed replacing terbium with aluminum in the computer, and the structure of [Al($C_{27}H_{15}O_6$)] was predicted. An OLi group was then introduced, MSINDO calculation was performed again, and the structure of [Al($C_{27}H_{15}O_7$Li)] was predicted. The structure is shown in FIG. 1. Based on the results, [Al($C_{27}H_{15}O_7$Li)] was found to have a one-dimensional channel structure in which metal complexes produced by coordination bonding between aluminum and an aromatic tricarboxylic acid represented by formula (3) were integrated in the c-axis direction.

(Identification of Porous Coordination Polymer)

Figure 2:
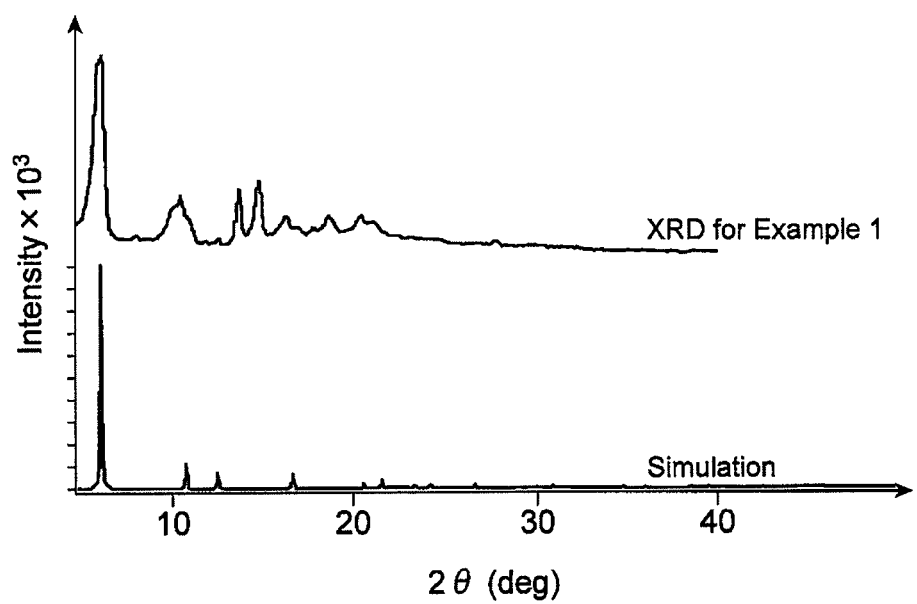
FIG. 2 is a diagram showing an XRD chart for the porous coordination polymer obtained in Example 1, and XRD simulation results predicted from the crystal structure of [Al($C_{27}H_{14}O_7Li$)].
Figure 3:
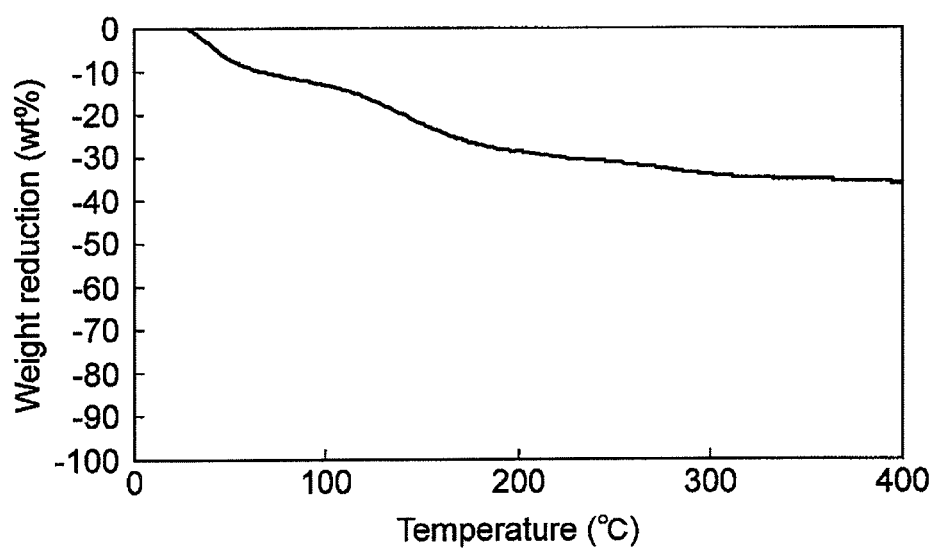
FIG. 3 is a TG chart for the porous coordination polymer obtained in Example 1.

The porous coordination polymer of Example 1 was analyzed by X-ray diffraction (XRD) and thermogravimetric analysis (TG). The obtained XRD chart is shown in FIG. 2, and the TG chart is shown in FIG. 3. FIG. 2 also shows the XRD pattern for [Al($C_{27}H_{15}O_7$ Li)], calculated using the results from MSINDO calculation. As seen in FIG. 2, the diffraction patterns for the porous coordination polymer of Example 1 and [Al($C_{27}H_{15}O_7$Li)] approximately matched. It was thus confirmed that the porous coordination polymer of Example 1 was [Al($C_{27}H_{15}O_7$Li)].

Figure 4:
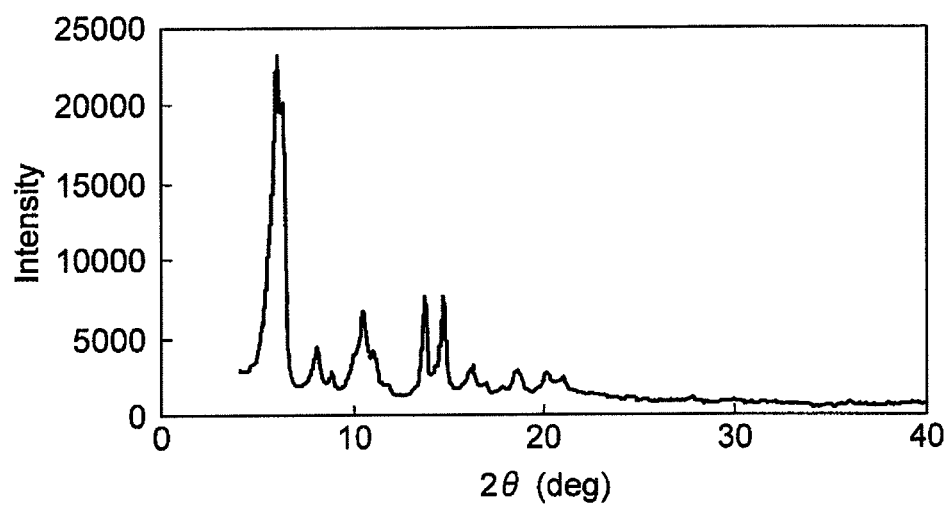
FIG. 4 is a XRD graph for the heat-dried porous coordination polymer obtained in Example 1.

The weight reduction in TG suggested that the composition of the porous coordination polymer of Example 1 was [Al($C_{27}H_{15}O_7$ Li)].3.5DMF. The 3.5DMF of [Al($C_{27}H_{15}O_6$)].3.5DMF can be easily removed by vacuum drying while heating. For example, 8 hours of vacuum drying while heating at 120° C. allows removal of the solvent. An XRD obtained after heat-drying in this manner is shown in FIG. 4. The XRD diffraction pattern for Example 1 shown in FIG. 4 approximately matched the diffraction pattern in FIG. 2. This confirmed that the backbone of the porous coordination polymer was supported even when the solvent had become incorporated into the pores of the porous coordination polymer.

Figure 5:
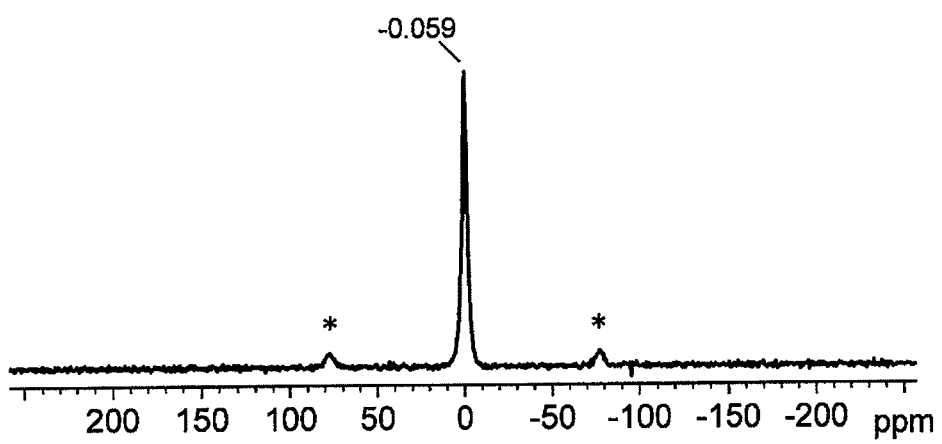
FIG. 5 is solid $^7$Li—NMR chart for the porous coordination polymer obtained in Example 1.

The porous coordination polymer of Example 1 was analyzed by solid $^7$Li—NMR measurement. FIG. 5 shows a solid $^7$Li—NMR chart. The results showed a peak observed at δ−0.059. This suggests that the mobility of Li is restricted to some degree. For lithium hydroxide alone, for example, the NMR peak is extremely sharp. It was thus demonstrated that the porous coordination polymer of Example 1 contained no lithium hydroxide, and Li had been introduced into the hydroxyl group ligands. A spinning-side-band(*) is observed in the solid $^7$Li—NMR chart shown in FIG. 5.

(Gas Adsorption Property)

Figure 6:
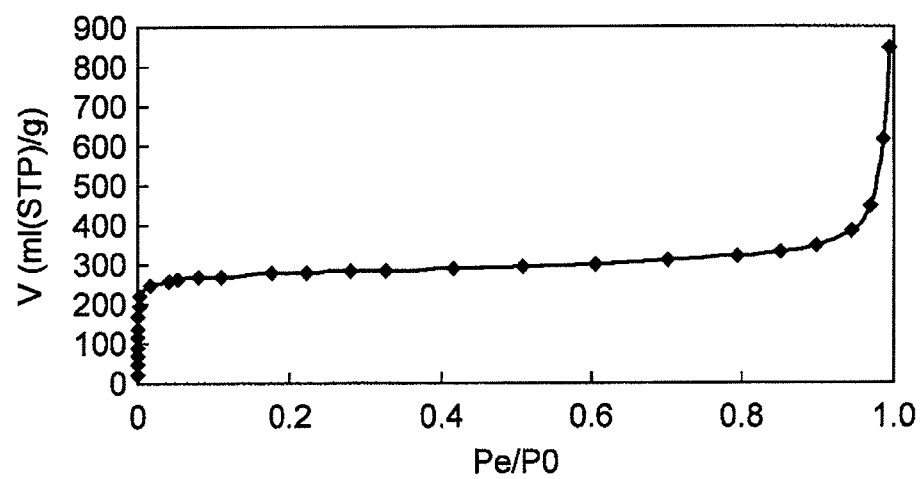
FIG. 6 is a nitrogen adsorption isotherm at 77K, for the porous coordination polymer obtained in Example 1.

The nitrogen adsorption, specific surface area and pore volume of the porous coordination polymer of Example 1 at a temperature of 77K were measured. BELSORP-max (trade name) by Bel Japan, Inc. was used for the measurement. The measurement was conducted with the portion of the sample tube containing the porous coordination polymer dipped in liquid nitrogen. The obtained absorption isotherm is shown in FIG. 6. The specific surface area, per gram of the porous coordination polymer of Example 1, calculated by the BET method, was 1103 m$^2$/g, and the pore volume calculated by the t-plot method was 0.384 cm$^3$.

Figure 7:
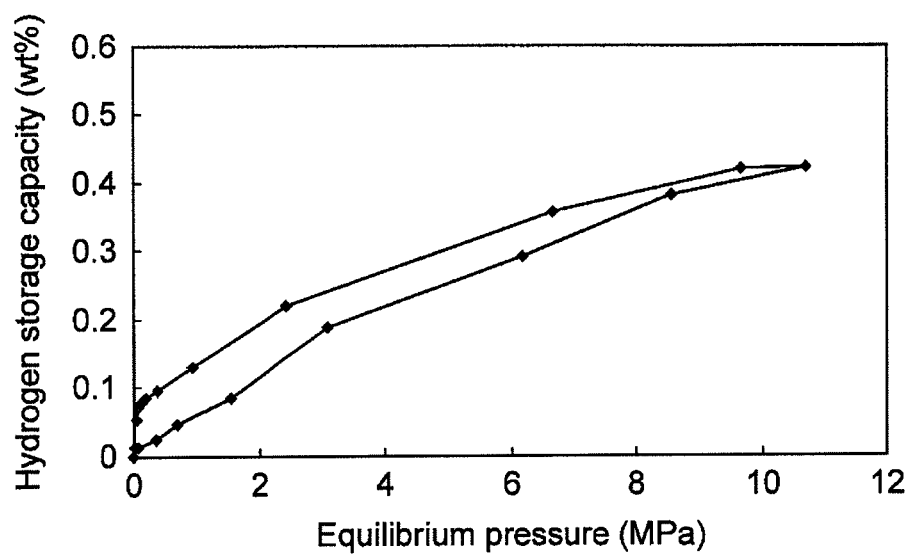
FIG. 7 is a graph showing the relationship between equilibrium pressure and hydrogen storage capacity at 303K for the porous coordination polymer obtained in Example 1.

The hydrogen storage capacity for the porous coordination polymer of Example 1 at 303K was measured. The hydrogen storage capacity was measured using a hydrogen storage capacity measuring apparatus by Rhesca Corp. The measurement was conducted with the portion of the sample tube containing the porous coordination polymer dipped in a water tank at 303K. FIG. 7 is a graph showing the relationship between hydrogen storage capacity and equilibrium pressure. For the porous coordination polymer of Example 1, the hydrogen storage capacity at a temperature of 303K and a hydrogen pressure of 10 MPa was 0.41 wt %.

Figure 8:
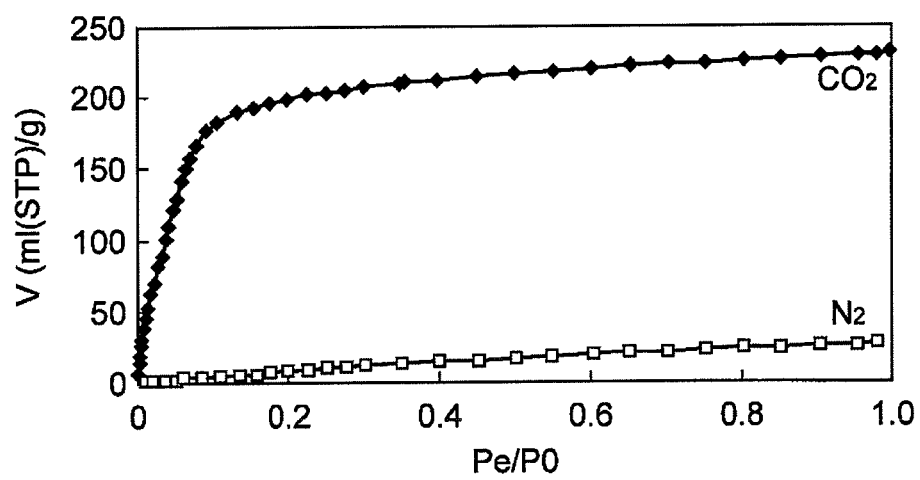
FIG. 8 shows carbon dioxide and nitrogen absorption isotherms at 195K, for the porous coordination polymer obtained in Example 1.

Also measured were the nitrogen and carbon dioxide adsorptions of the porous coordination polymer of Example 1 at a temperature of 195K and an adsorption gas pressure of 0.1 MPa. As a result, the nitrogen adsorption was 3.23 wt % and the carbon dioxide adsorption was 45.3 wt %, thereby confirming selective adsorption of carbon dioxide. BELSORP-max (trade name) by Bel Japan, Inc. was used for the measurement. The measurement was conducted with the portion of the sample tube containing the porous coordination polymer dipped in a dry ice-ethanol refrigerant. This confirmed that the porous coordination polymer of Example 1 can be used to separate nitrogen and carbon dioxide from a mixed gas of nitrogen and carbon dioxide at 195K. The obtained absorption isotherm is shown in FIG. 8.

Example 2

Porous Coordination Polymer Comprising Terbium Ion and Aromatic Tricarboxylic Acid Represented by Formula (3)

(Synthesis of Porous Coordination Polymer)

In a screw tube there were placed terbium nitrate hexahydrate by Mitsuwa Chemicals Co., Ltd. (507.6 mg, 1.25 mmol), 2,4,6-tris-(4-carboxyphenyl)phenol (567.0 mg, 1.25 mmol) and purified water (12.5 mL). A 2M water-soluble lithium hydroxide solution (1 mL) was then added to the screw tube and the mixture was stirred for 2 minutes. To this there was added cyclohexanol (12.5 mL) as a heated liquid, and the mixture was further stirred for 10 minutes. Next, TEFLON® packing was inserted in the screw tube and the cover closed, and the screw tube was placed in an autoclave by Taiatsu Techno and subjected to hydrothermal synthesis at 100° C. for 48 hours. On the following day, the contents of the screw tube were filtered, the obtained solid was rinsed twice with water (10 mL), and then rinsed twice with ethanol (10 mL) and twice with acetone (10 mL) and vacuum dried, to obtain a pale yellow product. (Yield: 784.1 mg)

(Identification of Porous Coordination Polymer)

Figure 9:
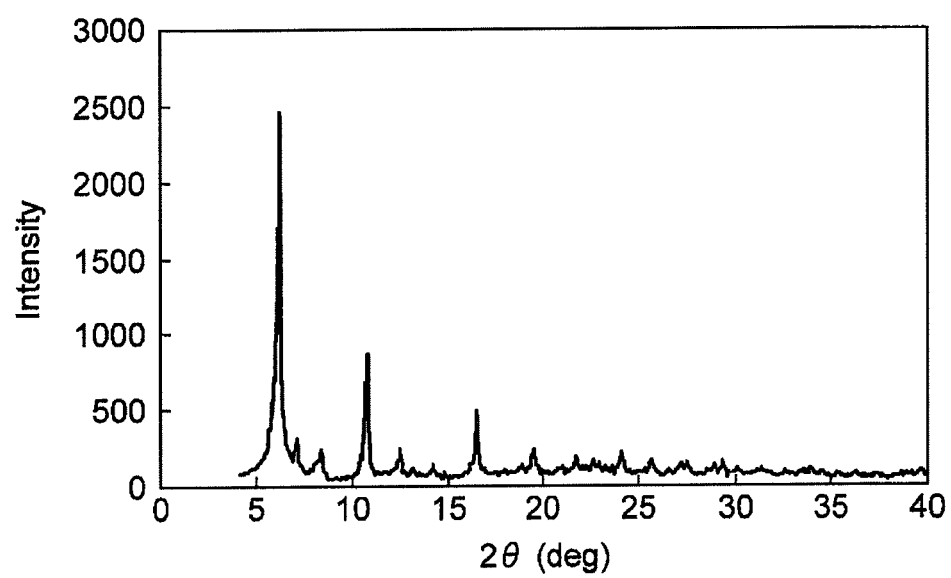
FIG. 9 is an XRD chart for the porous coordination polymer obtained in Example 2.
Figure 10:
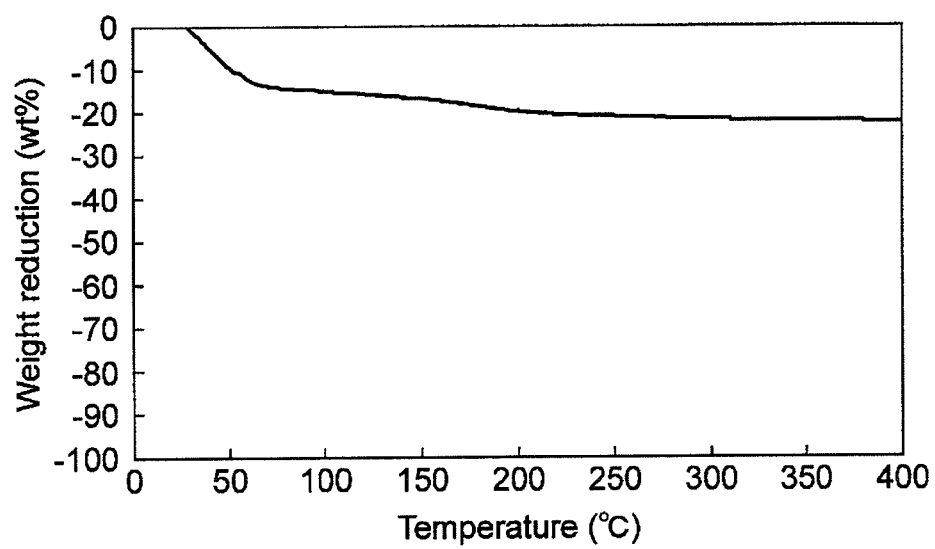
FIG. 10 is a TG chart for the porous coordination polymer obtained in Example 2.

The porous coordination polymer of Example 2 obtained as described above was analyzed by X-ray diffraction (XRD) and thermogravimetric analysis (TG) in the same manner as Example 1. The obtained XRD chart is shown in FIG. 9, and the TG chart is shown in FIG. 10. Upon comparing FIG. 9 with FIG. 2, an approximate match is seen between the diffraction patterns of the porous coordination polymer of Example 2 and [Tb($C_{27}H_{15}O_7Li$)]. This confirmed that the porous coordination polymer of Example 2 has the same structure as [Tb($C_{27}H_{15}O_7Li$)], i.e. that it has a structure with aluminum replaced by terbium. The weight reduction in TG shown in FIG. 10 suggested that the composition of the porous coordination polymer of Example 1 was [Tb($C_{27}H_{15}O_7Li$)].1.5$C_6H_{11}O$. For the complex of Example 2 as well, it was possible to easily remove cyclohexanol $C_6H_{11}O$ in the pores using the same method as Example 1.

(Gas Adsorption Property)

Figure 11:
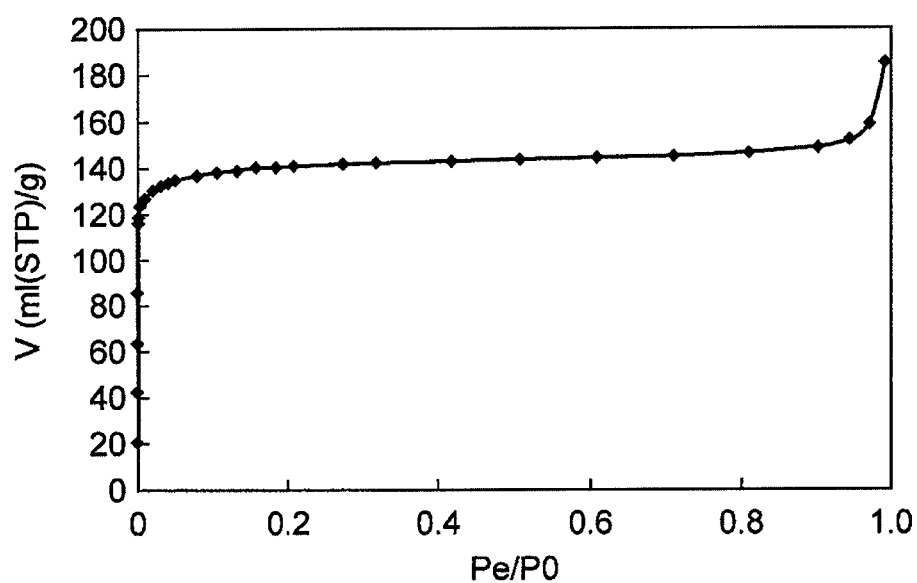
FIG. 11 is a nitrogen adsorption isotherm at 77K, for the porous coordination polymer obtained in Example 2.

The nitrogen adsorption and pore volume of the porous coordination polymer of Example 2 at a temperature of 77K were measured. BELSORP-max (trade name) by Bel Japan, Inc. was used for the measurements. The measurement was conducted with the portion of the sample tube containing the porous coordination polymer dipped in liquid nitrogen. The obtained absorption isotherm is shown in FIG. 11. The specific surface area of the porous coordination polymer of Example 2, calculated by the BET method, was 543 m$^2$, and the pore volume calculated by the t-plot method was 0.215 cm$^3$.

Figure 12:
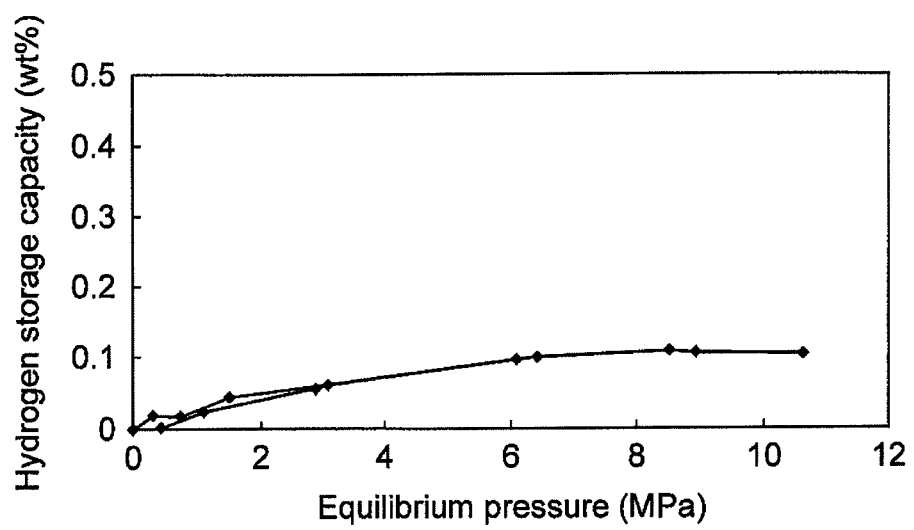
FIG. 12 is a graph showing the relationship between equilibrium pressure and hydrogen storage capacity at 303K for the porous coordination polymer obtained in Example 2.

The hydrogen storage capacity for the porous coordination polymer of Example 2 at 303K was measured in the same manner as Example 1. FIG. 12 is a graph showing the relationship between hydrogen storage capacity and equilibrium pressure. For the porous coordination polymer of Example 2, the hydrogen storage capacity at 303K and a hydrogen pressure of 10 MPa was 0.11 wt %.

Figure 13:
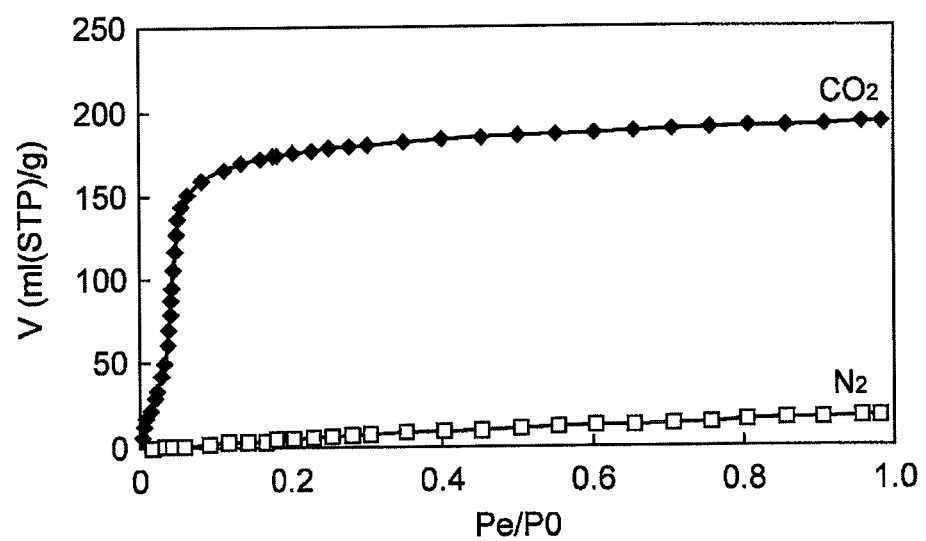
FIG. 13 shows carbon dioxide and nitrogen absorption isotherms at 195K, for the porous coordination polymer obtained in Example 2.

The nitrogen and carbon dioxide adsorptions of the porous coordination polymer of Example 2 were also measured in the same manner as Example 1, at a temperature of 195K and a carbon dioxide pressure of 0.1 MPa. As a result, the nitrogen adsorption was 2.2 wt % and the carbon dioxide adsorption was 37.8 wt %. The obtained absorption isotherm is shown in FIG. 13. This confirmed that the porous coordination polymer of Example 2 can be used to separate nitrogen and carbon dioxide from a mixed gas of nitrogen and carbon dioxide, similar to Example 1.

Comparative Example 1

Synthesis of Aluminum Ion and Porous Coordination Polymer Represented by Formula (5)

[Chemical Formula 5]

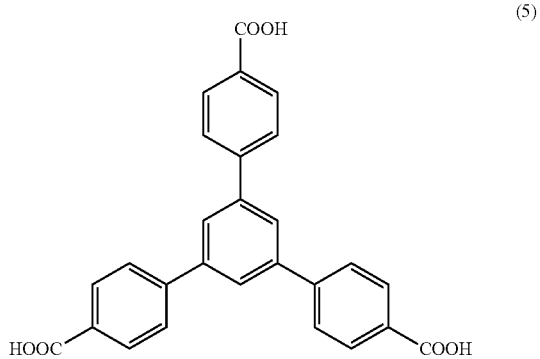

(5)

(Synthesis of Aromatic Carboxylic Acid Represented by Formula (5))

A mixture of 0.8 kg of 4-bromoacetophenone by Sigma-Aldrich Japan, KK., 40 ml of sulfuric acid and 1.2 kg of potassium disulfate was stirred at 180° C. for 18 hours. After stirring, 3.0 L of ethanol was added to the mixture, which was heated to reflux for 7 hours. It was then allowed to naturally cool to room temperature, producing a precipitate which was filtered out. After adding 3.0 L of water to the filtered precipitate and heating to reflux for 1 hour, the reaction mixture was allowed to naturally cool to room temperature. The reaction mixture was filtered and rinsed with 0.5 L of ethanol. In this manner there was obtained 0.58 kg of 1,3,5-tris(p-bromophenyl)benzene.

A solution comprising 0.58 kg of 1,3,5-tris(p-bromophenyl)benzene and 7.2 L of tetrahydrofuran was cooled to −65° C. under an argon gas atmosphere. A 1.6 mol/L butyllithium n-hexane solution (2.1 L) by Wako Pure Chemical Industries, Ltd. was then added dropwise at −65° C. to −60° C. After reaction at −65° C. for 1 hour, $CO_2$ gas was bubbled through for 1 hour at −65° C. to −60° C. A 2.5 L portion of 1N-hydrochloric acid was added dropwise to the reaction product, and the deposited precipitate was filtered out to obtain 0.40 g of a crude product of the aromatic carboxylic acid represented by formula (5). The crude product was rinsed with tetrahydrofuran and then with hexane and dried under reduced pressure to obtain 0.29 g of the aromatic carboxylic acid represented by formula (5).

(Synthesis and Identification of Porous Coordination Polymer)

After repeating the procedure described above several times, 1.0 g of the obtained aromatic carboxylic acid represented by formula (5), 0.86 g of aluminum nitrate nonahydrate by Kishida Chemical Co., Ltd., and N,N-diethylformamide by Tokyo Kasei Kogyo Co., Ltd. (50 mL) were placed in a carbon resin-coated polytetrafluoroethylene crucible produced by San-Ai Science Co., Ltd. The crucible was sealed with a stainless steel jacket, and the stainless steel jacket was dipped for 24 hours in an oil bath prepared to a temperature of 150° C. The crucible was then cooled to room temperature, and the white precipitate produced in the reaction mixture was filtered out to obtain 1.4 g of a porous coordination polymer. Identification was carried out in the same manner as Examples 1 and 2.

(Gas Adsorption Property)

Figure 14:
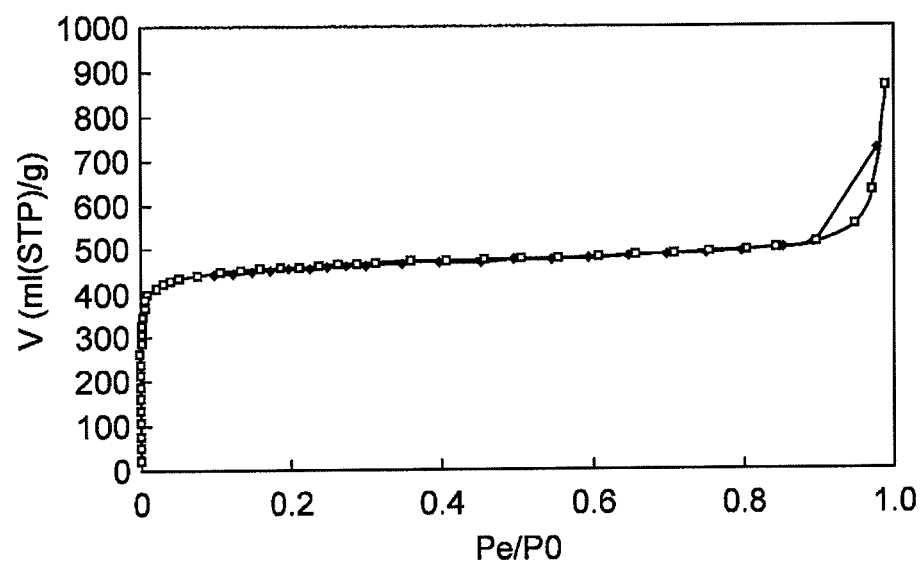
FIG. 14 is a nitrogen adsorption isotherm at 77K, for the porous coordination polymer obtained in Comparative Example 1.

The nitrogen adsorption and pore volume of the porous coordination polymer of Comparative Example 1 at a temperature of 77K were measured in the same manner as Examples 1 and 2. The obtained absorption isotherm is shown in FIG. 14. The specific surface area of the porous coordination polymer of Comparative Example 1, calculated by the BET method, was 1800 m$^2$, and the pore volume calculated by the t-plot method was 0.672 cm$^3$. The larger specific surface area and pore volume of the porous coordination polymer of Comparative Example 1 compared to the porous coordination polymer of Example 1 was due to a gain in space resulting from a lack of lithium alkoxide groups in the ligand.

Figure 15:
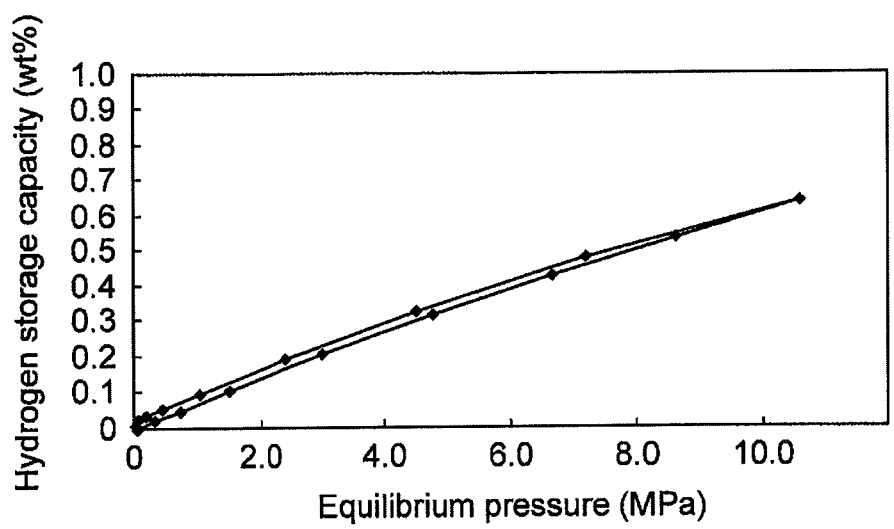
FIG. 15 is a graph showing the relationship between equilibrium pressure and hydrogen storage capacity at 303K for the porous coordination polymer obtained in Comparative Example 1.

The hydrogen storage capacity for the porous coordination polymer of Comparative Example 1 at a temperature of 303K was measured in the same manner as Examples 1 and 2. The relationship between the equilibrium pressure and hydrogen storage capacity is shown in FIG. 15. The hydrogen storage capacity at a temperature of 303K and a hydrogen pressure of 10 MPa was 0.60 wt %. More hydrogen could be stored than in the porous coordination polymer of Example 1 because of the larger pore volume.

The adsorption densities of the porous coordination polymers of Example 1 and Comparative Example 1 were calculated, for comparison of the "hydrogen affinity" of the pores in numerical terms. The adsorption density is the value of the hydrogen storage capacity divided by the pore volume, and it is expressed as the hydrogen storage capacity per 1 cm$^3$ of pore volume, with a larger value corresponding to higher affinity for hydrogen. The adsorption densities of Example 1 and Comparative Example 1 were 10.7 kg/m$^3$ and 8.9 kg/m$^3$, respectively. This confirmed that the porous coordination polymer of Example 1 had higher affinity for hydrogen than the porous coordination polymer of Comparative Example 1.

Comparative Example 2

Synthesis of Terbium Ion and Porous Coordination Polymer Represented by Formula (5)

(Synthesis and Identification of Porous Coordination Polymer)

In a screw tube there were placed terbium nitrate hexahydrate by Mitsuwa Chemicals Co., Ltd. (565.8 mg, 1.25 mmol), 2,4,6-tris-(4-carboxyphenyl)phenol (546.7 mg, 1.25 mmol) and purified water (12.5 mL). A 2M water-soluble sodium hydroxide solution (1.0 mL) was then added to the screw tube and the mixture was stirred for 2 minutes. Next, 12.5 mL of cyclohexanol was added to the screw tube as a heated liquid, and stirring was continued for 10 minutes. Next, TEFLON® packing was inserted in the screw tube and the cover closed, and the screw tube was placed in an autoclave by Taiatsu Techno and subjected to hydrothermal synthesis at 100° C. for 48 hours. On the following day, the contents of the screw tube were filtered, the obtained solid was rinsed with water (10 mL×2.5 mL×1), twice with ethanol (10 mL) and twice with acetone (10 mL) and vacuum dried, to obtain a white product. (Yield: 491.8 mg)

(Gas Adsorption Property)

Figure 16:
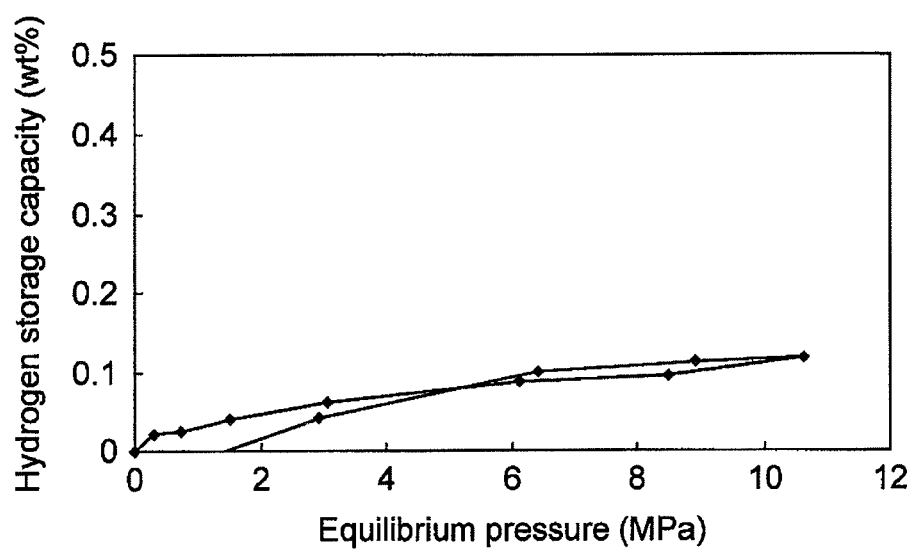
FIG. 16 is a graph showing the relationship between equilibrium pressure and hydrogen storage capacity at 303K for the porous coordination polymer obtained in Comparative Example 2.

The hydrogen storage capacity for the porous coordination polymer of Comparative Example 2 at a temperature of 303K was measured in the same manner as Examples 1 and 2. The relationship between the equilibrium pressure and hydrogen storage capacity is shown in FIG. 16. The hydrogen storage capacity at a temperature of 303K and a hydrogen pressure of 10 MPa was 0.11 wt %.

(Adsorption Density)

The adsorption densities of the porous coordination polymers of Example 2 and Comparative Example 2 were calculated to be 5.1 kg/m$^3$ and 3.1 kg/m$^3$, respectively, showing that the porous coordination polymer of Example 2 had higher affinity for hydrogen than Comparative Example 2. The value for the pore volume of Comparative Example 2 was calculated from the absorption isotherm reported in J. Am. Chem. Soc. 2005, 127, 12788-12789.

INDUSTRIAL APPLICABILITY

According to the invention it is possible to provide a porous coordination polymer having a high specific surface area and high pore volume, and improved affinity for gases (especially hydrogen gas), as well as a process for producing it, and a gas storage method and gas separation method using the porous coordination polymer. In particular, the porous coordination polymer of the invention has excellent hydrogen storage capacity at ordinary temperatures (for example, 303K), and is highly useful as a hydrogen storage material.

The invention claimed is:

1. A porous coordination polymer comprising:
   metal complexes formed by coordination bonding between a trivalent metal ion and an aromatic tricarboxylic acid represented by formula (1),
   wherein the porous coordination polymer has a pore structure formed by integration of a plurality of the metal complexes (1)

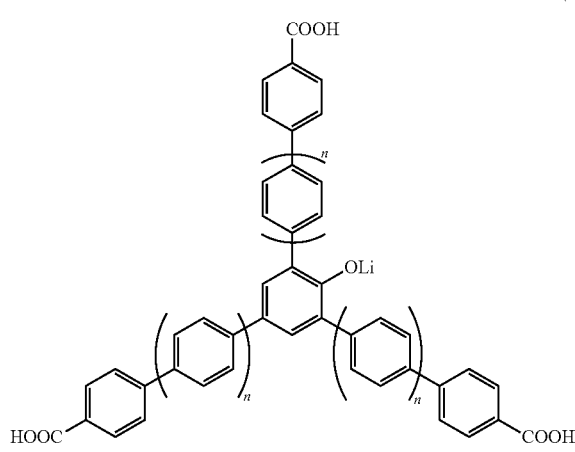

and wherein in formula (1), n represents an integer of 0 to 4.

2. The porous coordination polymer according to claim 1, wherein the pore volume is at least 0.1 cm³ per gram of the porous coordination polymer.

3. The porous coordination polymer according to claim 1, further comprising the metal complexes formed by coordination bonding between the trivalent metal ion and an aromatic tricarboxylic acid represented by formula (2)

(2)

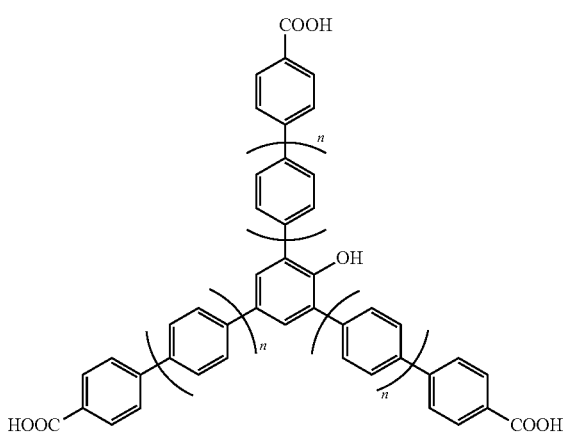

wherein in formula (2), n represents an integer of 0 to 4.

4. A process for producing a porous coordination polymer, comprising:
a first step in which there is prepared a liquid mixture comprising a trivalent metal ion, an aromatic tricarboxylic acid represented by formula (2), lithium hydroxide, and a co-solvent of an organic solvent and water, and
a second step in which the liquid mixture is heated to 100° C. or higher, to obtain a porous coordination polymer comprising metal complexes formed by coordination bonding between the trivalent metal ion and the aromatic tricarboxylic acid represented by formula (1), the porous coordination polymer having a pore structure formed by integration of a plurality of the metal complexes (2)

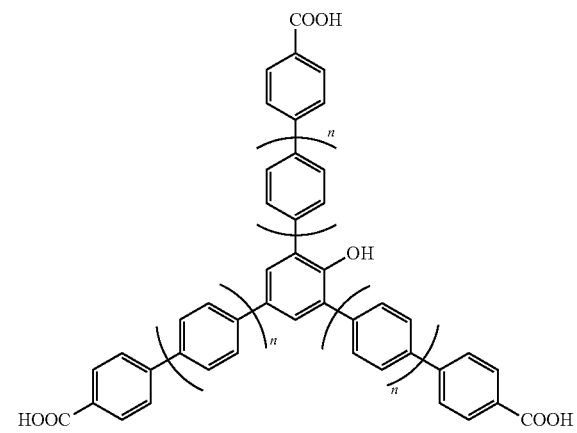

wherein in formula (2), n represents an integer of 0 to 4;

(1)

wherein in formula (1), n represents an integer of 0 to 4.

5. A process for producing a porous coordination polymer, comprising:
a first step in which an aromatic tricarboxylic acid represented by formula (2) and lithium hydroxide are stirred in a co-solvent of an organic solvent and water, to obtain a solution,
a second step in which a trivalent metal ion solution is added dropwise to the solution obtained in the first step and a precipitate is produced,
a third step in which the precipitate produced in the second step is filtered, and
a fourth step in which the precipitate that has been filtered in the third step is added to the co-solvent of an organic solvent and water, and heated to 100° C. or higher, to obtain a porous coordination polymer comprising metal complexes formed by coordination bonding between the trivalent metal ion and the aromatic tricarboxylic acid represented by formula (1), the porous coordination polymer having a pore structure formed by integration of a plurality of the metal complexes

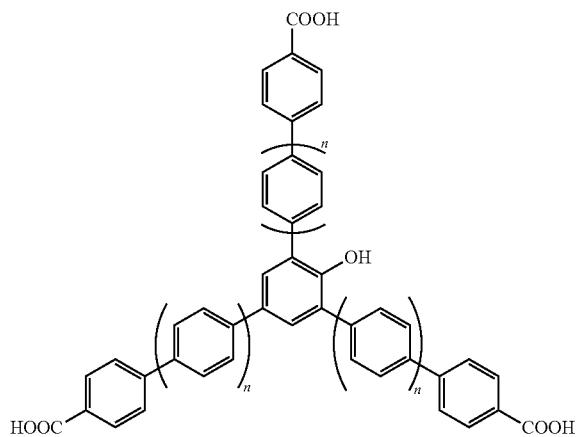

wherein in formula (2), n represents an integer of 0 to 4;

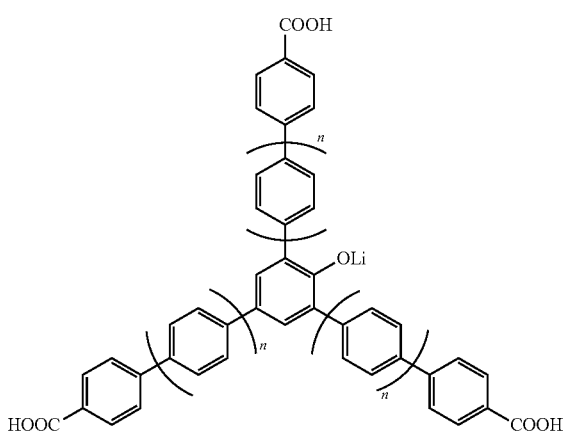

wherein in formula (1), n represents an integer of 0 to 4.

6. A gas storage method in which a gas is stored using a porous coordination polymer comprising metal complexes formed by coordination bonding between a trivalent metal ion and an aromatic tricarboxylic acid represented by formula (1), the porous coordination polymer having a pore structure formed by integration of a plurality of the metal complexes

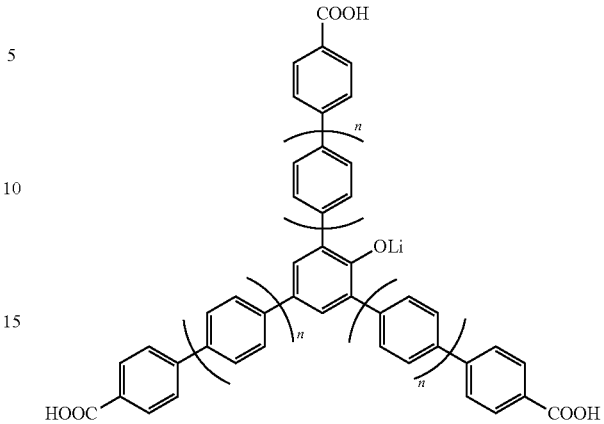

wherein in formula (1), n represents an integer of 0 to 4.

7. A gas separation method in which a gas is separated using a porous coordination polymer comprising metal complexes formed by coordination bonding between a trivalent metal ion and an aromatic tricarboxylic acid represented by formula (1), the porous coordination polymer having a pore structure formed by integration of a plurality of the metal complexes

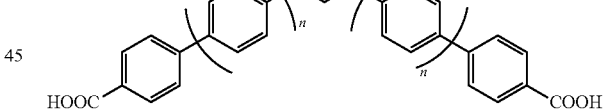

wherein in formula (1), n represents an integer of 0 to 4.

* * * * *